(12) United States Patent
Hewitt

(10) Patent No.: US 7,762,968 B1
(45) Date of Patent: Jul. 27, 2010

(54) CAST ACCESSORIES AND ASSOCIATED METHOD

(76) Inventor: Alice Hewitt, 402 Jerry St., Tallulah, LA (US) 71282

( * ) Notice: Subject to any disclaimer, the term of this patent is extended or adjusted under 35 U.S.C. 154(b) by 144 days.

(21) Appl. No.: 11/804,358

(22) Filed: May 19, 2007

(51) Int. Cl.
*A61F 5/00* (2006.01)
(52) U.S. Cl. .......................................... 602/3
(58) Field of Classification Search .............. 602/3; 2/59, 239, 61
See application file for complete search history.

(56) References Cited

U.S. PATENT DOCUMENTS

| | | | | |
|---|---|---|---|---|
| 2,949,912 | A * | 8/1960 | Shapiro | 602/11 |
| 3,497,875 | A * | 3/1970 | Rivera | 2/239 |
| 5,016,648 | A * | 5/1991 | Brown et al. | 128/846 |
| 2002/0068891 | A1 * | 6/2002 | Weathers | 602/48 |
| 2004/0092852 | A1 * | 5/2004 | Kruss | 602/21 |
| 2006/0287623 | A1 * | 12/2006 | Beck et al. | 602/3 |

* cited by examiner

*Primary Examiner*—Kim M Lewis

(57) ABSTRACT

The first protective sleeves are sized for fitting a foot cast. Each sleeve includes a bottom and top end. Each of the first protective sleeves also includes a uniform thickness, and a pad. A bottom end is closed and shelters the user foot. A second one of the first protective sleeves includes an ancillary extension and an elastic strap. A third one of the first protective sleeves includes a first and orifice. The second protective sleeves are sized for fitting over an arm cast. Each of the second protective sleeves has an open proximal end and a uniform thickness. One of the second protective sleeves includes a distal end provided with first and second orifices. A second of the second protective sleeves includes a glove. A third one of the second protective sleeves includes a glove with a plurality of spaced ducts, an ancillary extension, and an elastic strap.

12 Claims, 12 Drawing Sheets

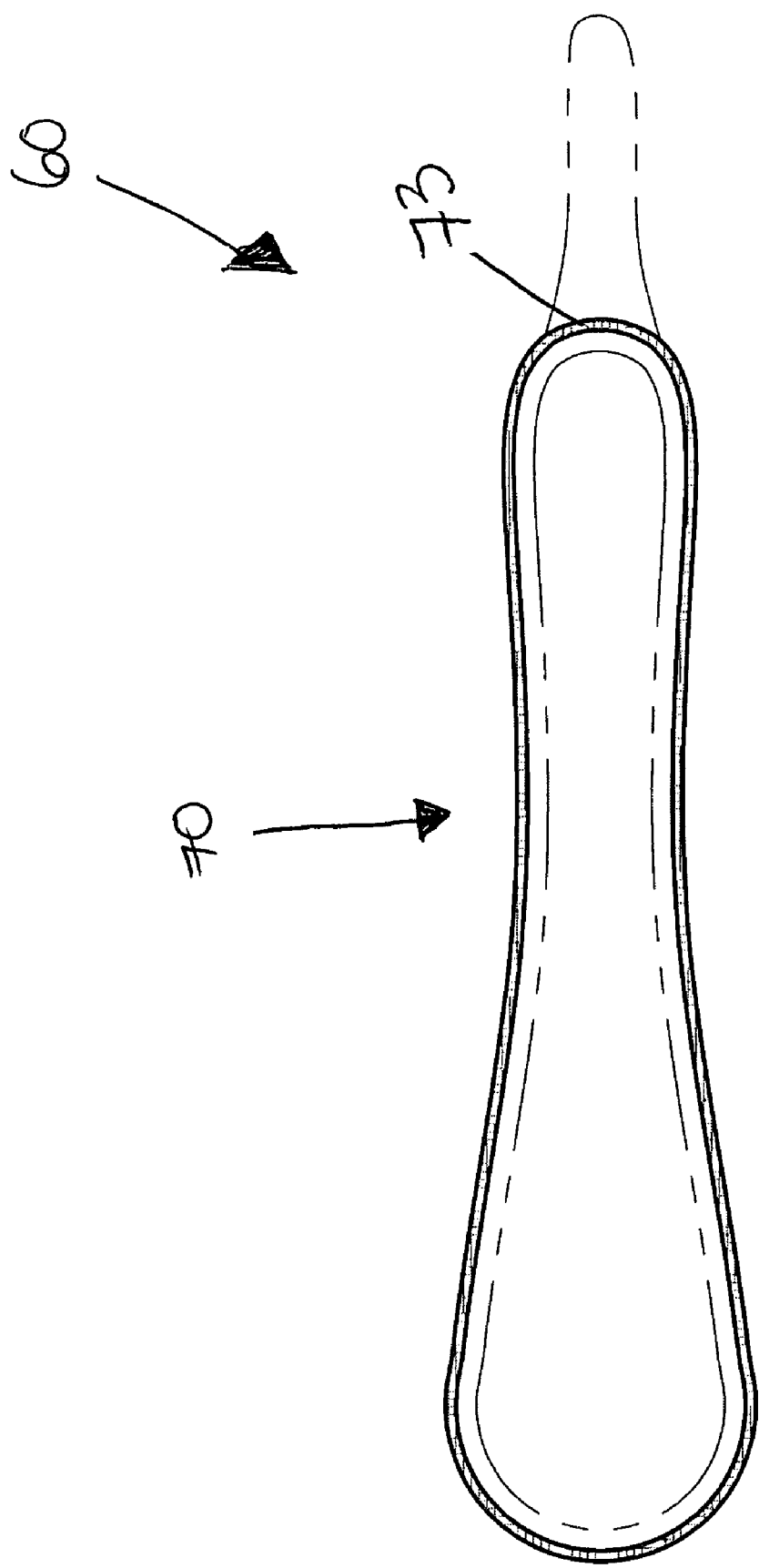

CAST ACCESSORIES AND ASSOCIATED METHOD

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to cast protection, and more specifically, to cast accessories for shielding existing foot and arm casts worn by a user during a healing period.

2. Prior Art

From a slip on the ice to the unsuspected fall of a nursing home resident, there are many ways to break one or more bones. Doctors and nurses generally treat broken bones by setting them and putting the limb in a cast. Like other treatments which come with a list of "instructions," casting is no different. For example, casts should not get wet. Though a few modern casting materials like fiberglass and water proof padding allows people this luxury, this is not yet the norm, and there are some circumstances in which this type of material cannot be used.

People who have casts will generally spend several weeks resting. Lack of use of an arm or leg can cause atrophy. In addition to taking its toll on muscles, there are mental stresses associated with casts. Immobility, restriction, pain and physical strain may cause the individual to become irritable, withdrawn or just frustrated and bored. For trauma victims, recuperation from injuries can also include emotional distress and even depression.

U.S. Pat. No. 6,126,621 to Aceves teaches a cast covering apparatus for effectively and comfortably covering an extremity of the body that includes a cover member having a cuff assembly at an open end, an absorbent interior layer, and a plurality of cinch assemblies. Unfortunately, this prior art example only provides a user temporary coverage and is not designed to be worn throughout the day in a visually pleasing manner.

U.S. Pat. No. 6,047,403 to Juozaitis teaches a decorative cast covering for a full leg cast. The covering is comprised of an elongated, generally cylindrical sleeve having an upper end and a lower end and a first elastomeric band fixed to the cast covering adjacent to the lower end. In this way, the lower end can be securely fastened by the elastomeric band to the bottom of the leg cast. The decorative cast covering further comprises a pocket secured along the generally cylindrical sleeve. Unfortunately, this prior art example is designed only for covering a leg cast and provides no benefit to users with casts on other areas of the body.

U.S. Pat. No. 4,454,872 teaches a wrap-around protective device for the human toes when the foot is encased in an orthopedic cast. The cast is comprised of a main part called a wrap which is positioned against the outer surface of the cast in a horizontal plane, from one ankle bone forward, arcing around the toes, and backward to the ankle bone on the other side of the encased foot. Such a wrap is located fore and aft by two cross-pieces fastened to the wrap called bows which are arcuately shaped to fit the contour of the underside of the cast in order to fit tightly against the front and rear surfaces of the rubber protrusion beneath the cast. The entire unit is removably held firm to the cast by means of laces that are fastened to the toe protector and tied together at the top surface of the part of the cast covering the foot. Unfortunately, this prior art example is only designed to protect casting of the foot and provides a user no benefit when other areas of the body are encased.

Accordingly, the present invention is disclosed in order to overcome the above noted shortcomings. The present invention satisfies such a need by providing apparatuses that are convenient and easy to use, lightweight yet durable in design, and designed for shielding existing foot and arm casts worn by a user during a healing period.

These apparatuses provide an easy-to use, practical way of protecting an arm or leg cast. In this way, activities of daily living during this healing period are made simpler. These sleeves boots and socks effectively assist in meeting doctor's recommendations regarding daily care of the cast, which typically should stay dry and clean. The elastic bands incorporated into the sleeve and boot enable the user to quickly and easily slip the cast accessories on and off. In addition, the adjustable strap provides a custom-lie, snug fit. The cast accessories are also available in a wide array of colors. These cast accessories also offer significant safety features, such as the rubber treading, which enable the user to ambulate and shower safely. The present invention is simple to use, inexpensive, and designed for repeated use.

BRIEF SUMMARY OF THE INVENTION

In view of the foregoing background, it is therefore an object of the present invention to provide an apparatus for shielding existing foot and arm casts worn by a user during a healing period. These and other objects, features, and advantages of the invention are provided by cast accessories.

The first apparatuses are a plurality of first protective sleeves suitably sized and shaped for fitting over an entire surface area of an existing foot cast. Each sleeve conveniently includes a bottom end removably positioned over an entire foot of the user and further has an open top end situated subjacent to a knee of the user.

Each of the first protective sleeves also includes a uniform thickness throughout an entire surface area thereof that effectively maintains direct contact with the entire outer surface of the existing foot cast.

Each of the first protective sleeves further includes a pad directly engaged with a bottom surface of the bottom end. Such a pad advantageously extends downwardly from the bottom end and forms a barrier between a ground surface and the bottom end of the first protective sleeves such that the pad is intercalated between the bottom end of the first protective sleeves and the ground surface during walking procedures. A bottom end of a first one of the first protective sleeves is conveniently closed and completely shelters the user foot from external fluids and debris.

A second one of the first protective sleeves includes an ancillary extension monolithically formed with the open top end thereof. Such an ancillary extension effectively maintains direct contact with epithelial tissue of the user and is spaced from the existing foot cast. The ancillary extension has a diameter smaller than a diameter of the open top end for advantageously assisting to anchor the first one of the first protective sleeves above an upper most end of the foot cast during extended time periods. An elastic strap is securely wrapped about the ancillary extension in such a manner that the elastic strap conveniently maintains a water-tight seal against the epithelial of the user and thereby prevents water from seeping into the existing foot cast. Such an elastic strap is effectively detachable from the first one of the first protective sleeves.

A third one of the first protective sleeves includes a first orifice formed within the bottom end thereof and a second orifice formed within the pad associated therewith. Each of the first and second orifices are vertically aligned and in direct communication for advantageously allowing an existing protective protrusion of the existing foot cast to penetrate outwardly from the second one of the first protective sleeves and thereby absorbs impact forces exerted on the foot of the user during walking procedures.

The second apparatuses are a plurality of second protective sleeves suitable sized and shaped for conveniently fitting over an entire surface area of the existing arm cast. Each of the second protective sleeves has an open proximal end situated above an arm of the user. Each of the second protective sleeves further has a uniform thickness throughout an entire surface area thereof and effectively maintains direct contact with the entire outer surface of the existing arm cast.

A first one of the second protective sleeves includes a distal end provided with first and second orifices formed therein. The first orifice is advantageously positioned along a top surface of the distal end and the second orifice is positioned along a lateral surface of the distal end. A thumb of the user is conveniently passed through the first orifice and remaining metacarpals of the user are passed through the second orifice.

A second one of the second protective sleeves effectively includes a glove monolithically formed with a distal end thereof and is removably positioned over an entire surface area of a hand of the user for prohibiting water from contacting the user epithelial tissue. Such a glove includes a plurality of spaced ducts independently fitted over each metacarpal of the user hand for advantageously allowing mobile movement of the metacarpals.

A third one of the second protective sleeves conveniently includes a glove monolithically formed with a distal end thereof and is removably positioned over an entire surface area of a hand of the user for prohibiting water from contacting the user epithelial tissue. Such a glove effectively includes a plurality of spaced ducts independently fitted over each metacarpal of the user hand for allowing mobile movement of the metacarpals. The glove further includes an ancillary extension monolithically formed with the proximal end. Such an ancillary section advantageously maintains direct contact with epithelial tissue of the user and is spaced from the existing arm cast. The ancillary section has a diameter smaller than a diameter of the proximal end for assisting to anchor the third one of the second protective sleeves above an upper most end of the existing arm cast during extended time periods. An elastic strap is securely wrapped about the ancillary extension in such a manner that the elastic strap conveniently maintains a water-tight seal against the epithelial of the user and thereby prevents water from seeping into the existing arm cast.

A method for shielding existing foot and arm casts worn by a user during a healing period includes the steps of: providing a plurality of first protective sleeves; providing a plurality of second protective sleeves; and selecting an appropriate sleeve from the first and second pluralities of protective sleeves respectively. If the selected sleeve is chosen from the first protective sleeves, then the method includes the steps of: fitting the selected sleeve over an entire surface area of the existing foot cast by removably positioning a bottom end of the selected protective sleeve over an entire foot of the user and further by situating an open top end of the selected protective sleeve subjacent to a knee of the user. If the selected sleeve is chosen from the second protective sleeves, then the method includes the steps of: fitting the selected sleeve over an entire surface area of the existing arm cast by situating an open proximal end of the selected sleeve above an arm of the user.

When a user selects among the first protective sleeves for use, the method further includes the steps of: maintaining direct contact with the entire outer surface of the existing foot cast by positioning a uniform thickness of the selected protective sleeve against the existing foot cast; and directly engaging a pad to a bottom surface of the bottom end of the selected protective sleeve. Such a pad extends downwardly from the bottom end and forms a barrier between a ground surface and the bottom end of the selected protective sleeve such that the pad is intercalated between the bottom end of the selected protective sleeve and the ground surface during walking procedures.

The method in using the first set of protective sleeves further includes the steps of providing an ancillary extension monolithically formed with the open top end of the selected protective sleeve by ensuring that the ancillary extension maintains direct contact with epithelial tissue of the user and remains spaced from the existing foot cast. Such an ancillary extension has a diameter smaller than a diameter of the open top end for assisting to anchor the selected protective sleeve above an upper most end of the foot cast during extended time periods. The steps further include: securely wrapping an elastic strap about the ancillary extension in such a manner that the elastic strap maintains a water-tight seal against the epithelial of the user and thereby prevents water from seeping into the existing foot cast; and detaching the elastic strap from the selected protective sleeve after a healing process is completed.

The method in using the first set of protective sleeves further includes the steps of: forming a first orifice within the bottom end of the selected protective sleeve; and forming a second orifice within the pad associated therewith. Such orifices are vertically aligned and in direct communication for allowing an existing protective protrusion of the existing foot cast to penetrate outwardly from the selected protective sleeve and thereby absorb impact forces exerted on the foot of the user during walking procedures.

The method in using the second set of protective sleeves includes the steps of: forming first and second orifices within a distal end of the selected protective sleeve. Such a first orifice is positioned along a top surface of the distal end and such a second orifice is positioned along a lateral surface of the distal end.

The method in using the second set of protective sleeves further includes the steps of: passing a thumb of the user through the first orifice; passing remaining metacarpals of the user through the second orifice; providing a glove that is monolithically formed with a distal end of the selected protective sleeve; and removably positioning the glove over an entire surface area of a hand of the user for prohibiting water from contacting the user epithelial tissue. Such a glove includes a plurality of spaced ducts independently fitted over each metacarpal of the user hand for allowing mobile movement of the metacarpals.

The method in using the second set of protective sleeves further includes the steps of providing an ancillary extension monolithically formed with a proximal end of the selected protective sleeve by ensuring that the ancillary extension maintains direct contact with epithelial tissue of the user and remains spaced from the existing arm cast. Such an ancillary extension has a diameter smaller than a diameter of the proximal end for assisting to anchor the selected protective sleeve above an upper most end of the arm cast during extended time periods. The steps further include: securely wrapping an elastic strap about the ancillary extension in such a manner that the elastic strap maintains a water-tight seal against the epithelial of the user and thereby prevents water from seeping into the existing arm cast; and detaching the elastic strap from the selected protective sleeve after a healing process is completed.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 12 is a cross sectional view of a third one of the arm protective sleeve taken along line 12-12 as shown in FIG. 11.

DETAILED DESCRIPTION OF THE INVENTION

Figure 1:
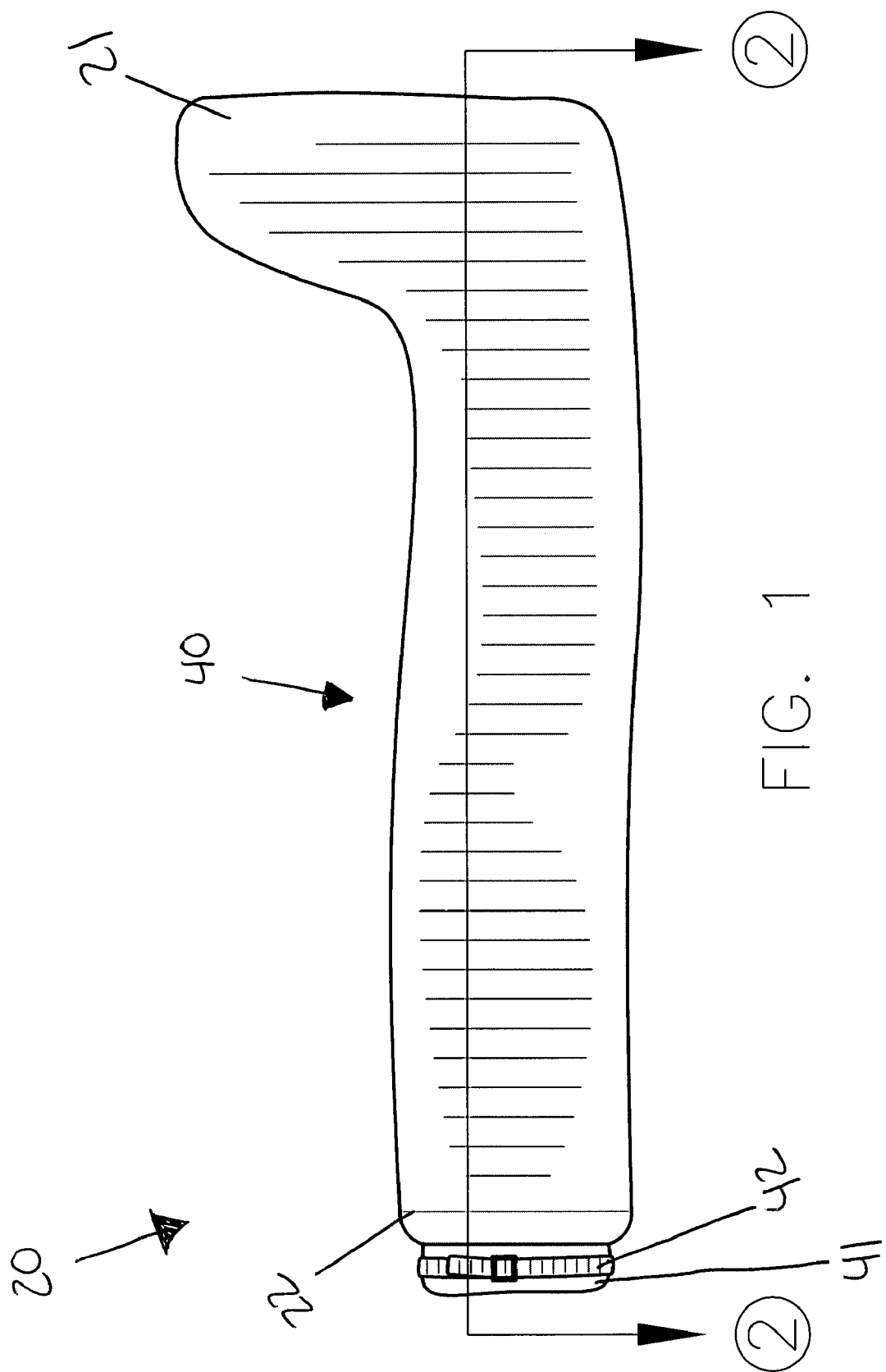
FIG. 1 is a side elevational view showing a second one of the foot protective sleeves in accordance with the present invention.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The apparatuses of this invention are referred to generally in FIGS. 1-12 by the reference numerals 20 and 60 and are intended to protect cast accessories. It should be understood that the apparatuses 20 and 60 may be used to protect many different types of casts and should not be limited to protecting only those types of casts described herein.

Referring initially to FIGS. 1-6, the first apparatuses are a plurality of first protective sleeves suitably sized and shaped for fitting over an entire surface area of an existing foot cast. Each sleeve conveniently includes a bottom end 21 removably positioned over an entire foot of the user and further has an open top 22 end situated subjacent to a knee of the user. Each of the first protective sleeves also includes a uniform thickness throughout an entire surface area thereof that effectively maintains direct contact with the entire outer surface of the existing foot cast. Since the protective covering provides full coverage of the cast the cast remains effectively shielded from outside contaminants such as dirt and water.

Figure 5:
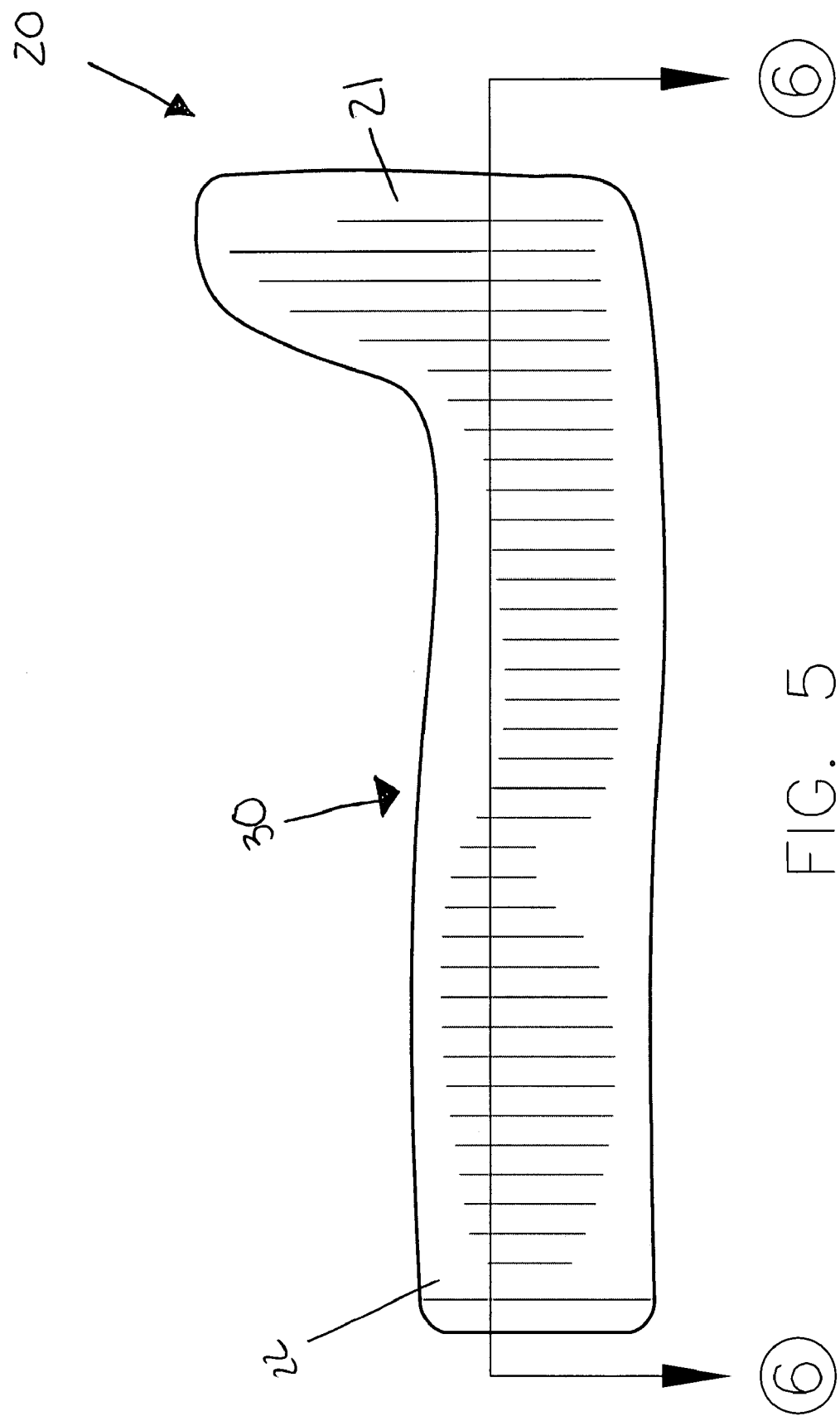
FIG. 5 is a side elevational view showing a first one of the foot protective sleeves in accordance with the present invention.
Figure 6:
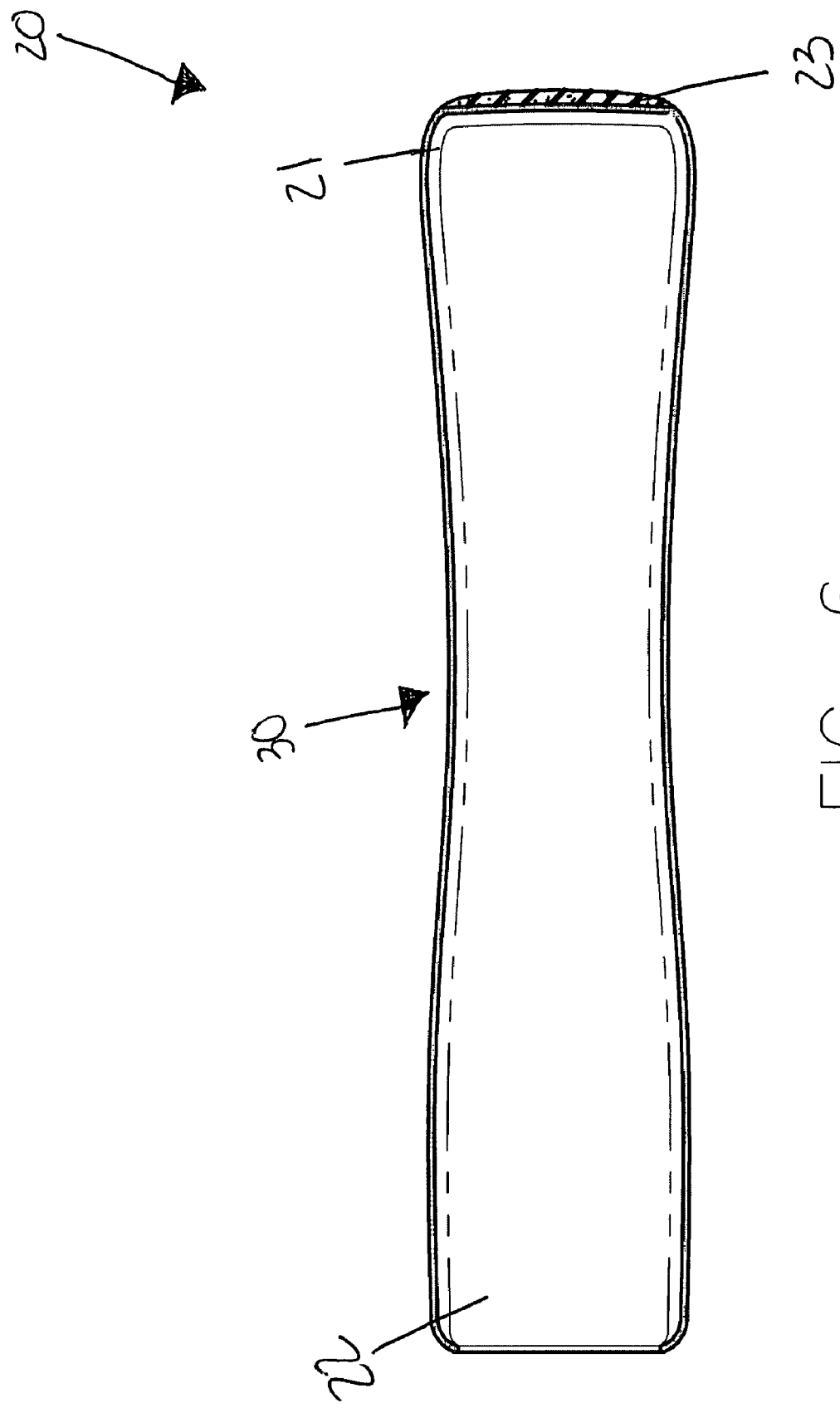
FIG. 6 is a cross sectional view of a first one of the foot protective sleeves taken along line 6-6 as shown in FIG. 5.

Referring again to FIGS. 1-6, each of the first protective sleeves 20 further includes a pad 23 directly, without the use of intervening elements, engaged with a bottom surface of the bottom end. Such a pad 23 advantageously extends downwardly from the bottom end and forms a barrier between a ground surface and the bottom end of the first protective sleeves 20 which is essential such that the pad 23 is intercalated between the bottom end of the first protective sleeves 20 and the ground surface during walking procedures. Referring to FIGS. 5 and 6, a bottom end 21 of a first one of the first protective sleeves 30 is conveniently closed and completely shelters the user foot from external fluids and debris. The pad 23 prevents the protective sleeve from the regular wear and tear associated with walking and thereby ensures that the cast will remain shielded from contact with the ground surface.

Figure 2:
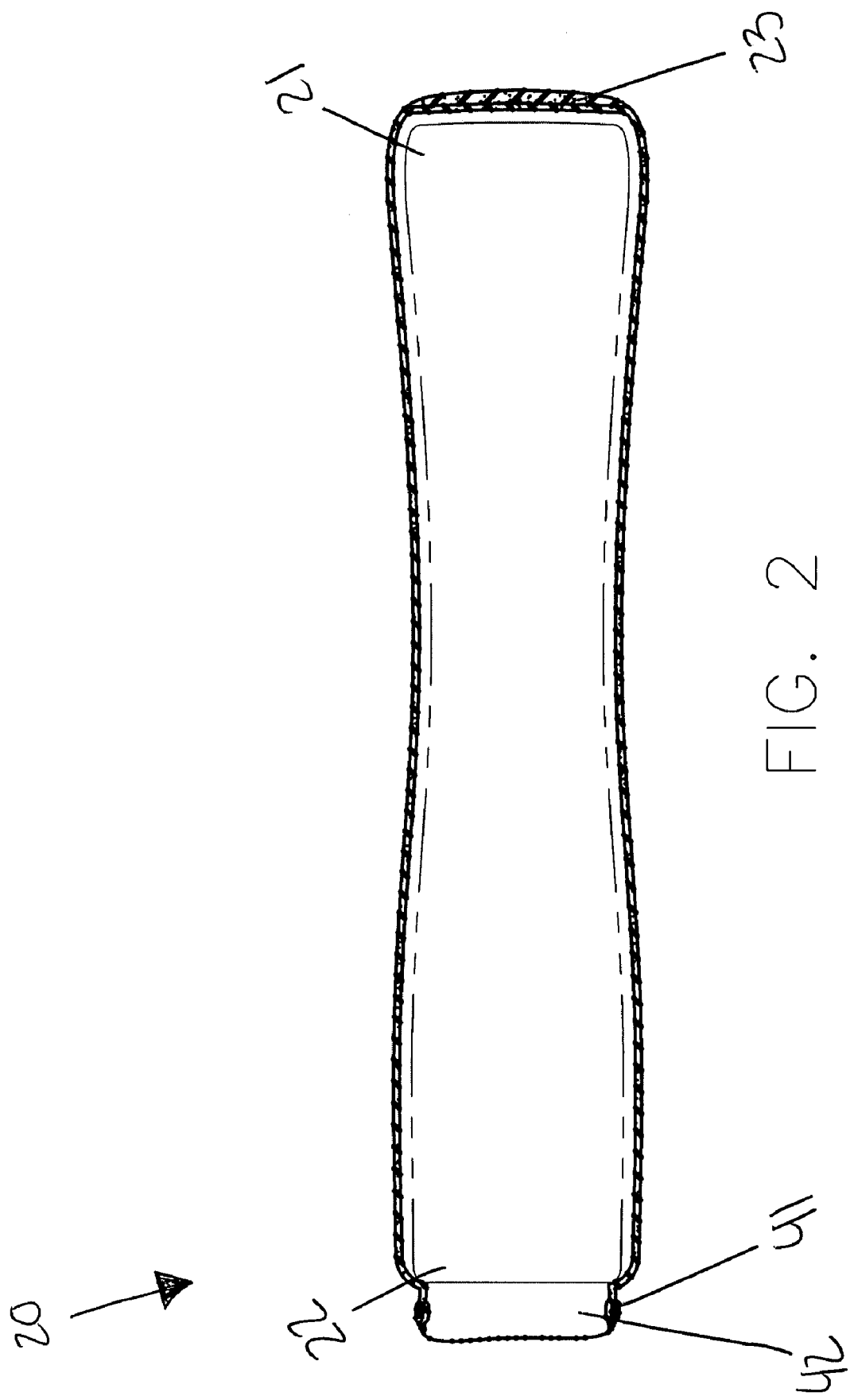
FIG. 2 is a cross sectional view of a second one of the foot protective sleeves taken along line 2-2 as shown in FIG. 1.

Referring to FIGS. 1 and 2, a second one of the first protective sleeves 40 includes an ancillary extension 41 monolithically formed with the open top end 22 thereof. Such an ancillary extension 41 effectively maintains direct contact with epithelial tissue of the user and is spaced from the existing foot cast. The ancillary extension 41 has a diameter smaller than a diameter of the open top end for advantageously assisting to anchor the first one of the first protective sleeves above an upper most end of the foot cast during extended time periods. An elastic strap 42 is securely wrapped about the ancillary extension in such a manner that the elastic strap 42 conveniently maintains a water-tight seal against the epithelial of the user and thereby prevents water from seeping into the existing foot cast. Such an elastic strap 42 is effectively detachable from the first one of the first protective sleeves 30. The elastic 42 strap prevents the protective covering from shifting from its proper position and thereby allows a user to travel extensively without losing the protection of the cast accessories.

Figure 3:
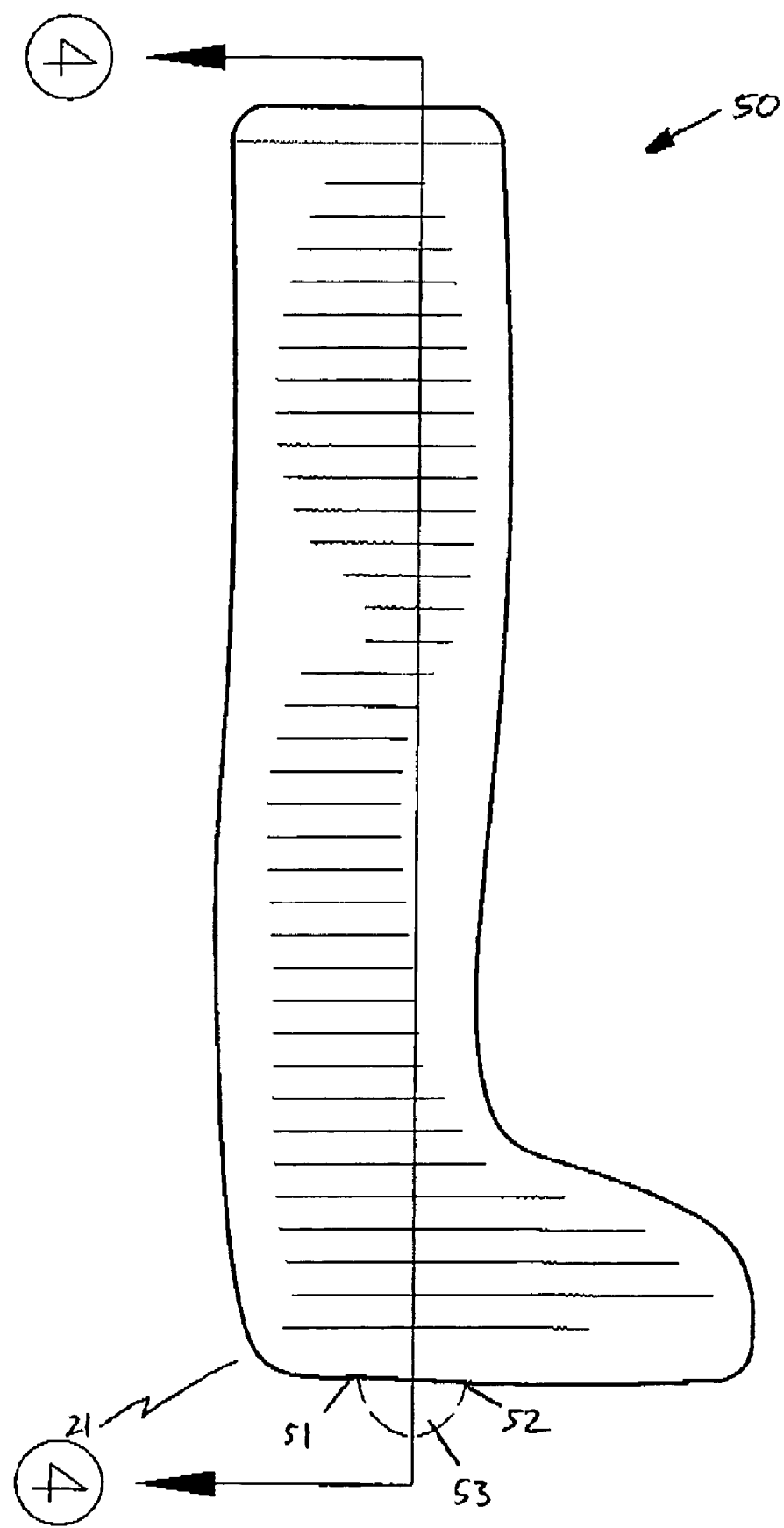
FIG. 3 is a side elevational view showing a third one of the foot protective sleeves in accordance with the present invention.
Figure 4:
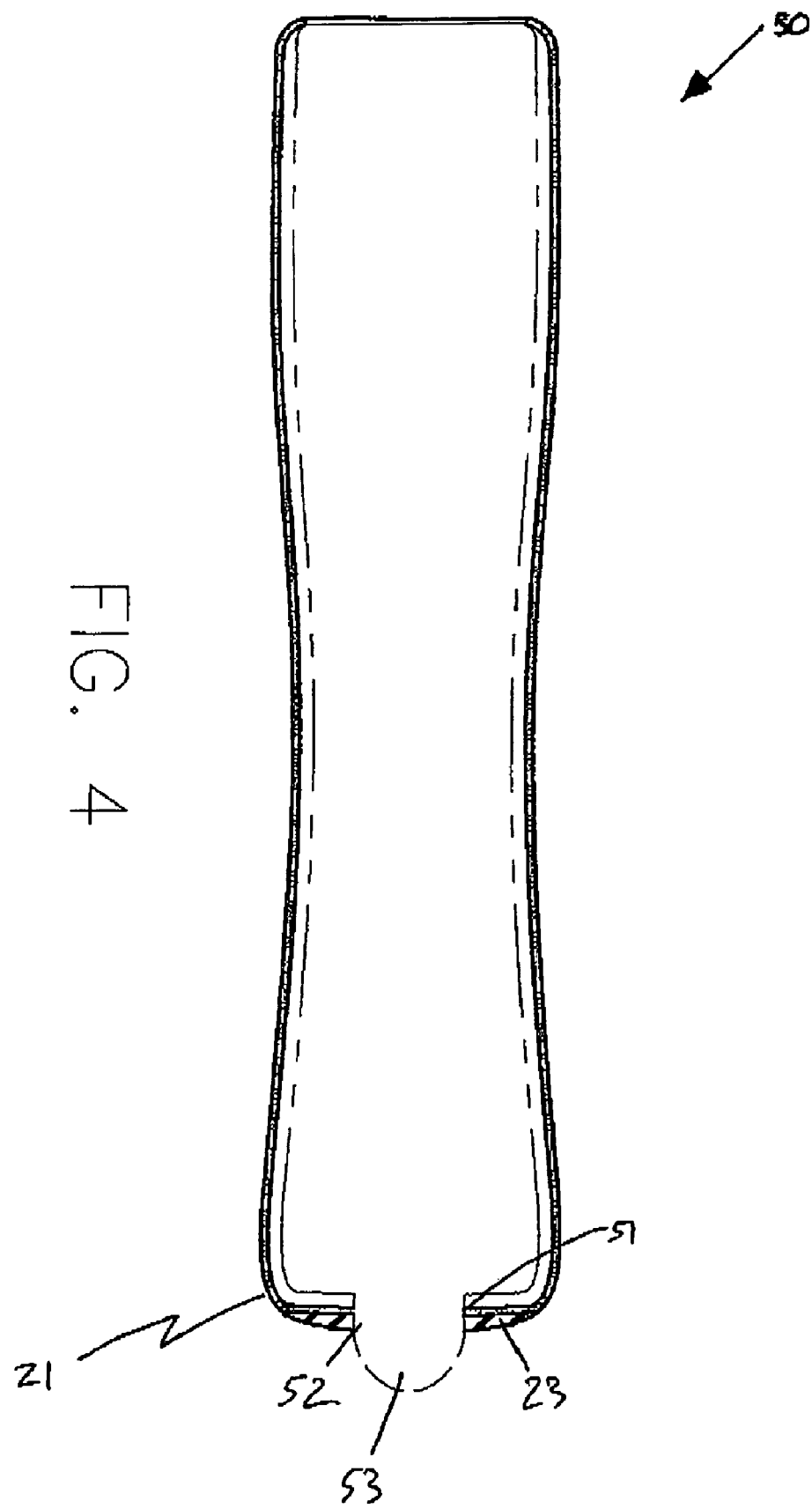
FIG. 4 is a cross sectional view of a third one of the foot protective sleeves taken along line 4-4 as shown in FIG. 3.

Referring to FIGS. 3 and 4, a third one of the first protective sleeves 50 includes a first orifice 51 formed within the bottom end 21 thereof and a second orifice 52 formed within the pad 23 associated therewith. Each of the first and second orifices 51, 52 are vertically aligned and in direct communication for advantageously allowing an existing protective protrusion 53 of the existing foot cast to penetrate outwardly from the second one of the first protective sleeves 30 and thereby absorbs impact forces exerted on the foot of the user during walking procedures.

Referring to FIGS. 7-12, the second apparatuses are a plurality of second protective sleeves 60 suitable sized and shaped which is critical for conveniently fitting over an entire surface area of the existing arm cast. Each of the second protective sleeves has an open proximal end 61 situated above an arm of the user. Each of the second protective sleeves further has a uniform thickness throughout an entire surface area thereof and effectively maintains direct contact with the entire outer surface of the existing arm cast.

Figure 11:
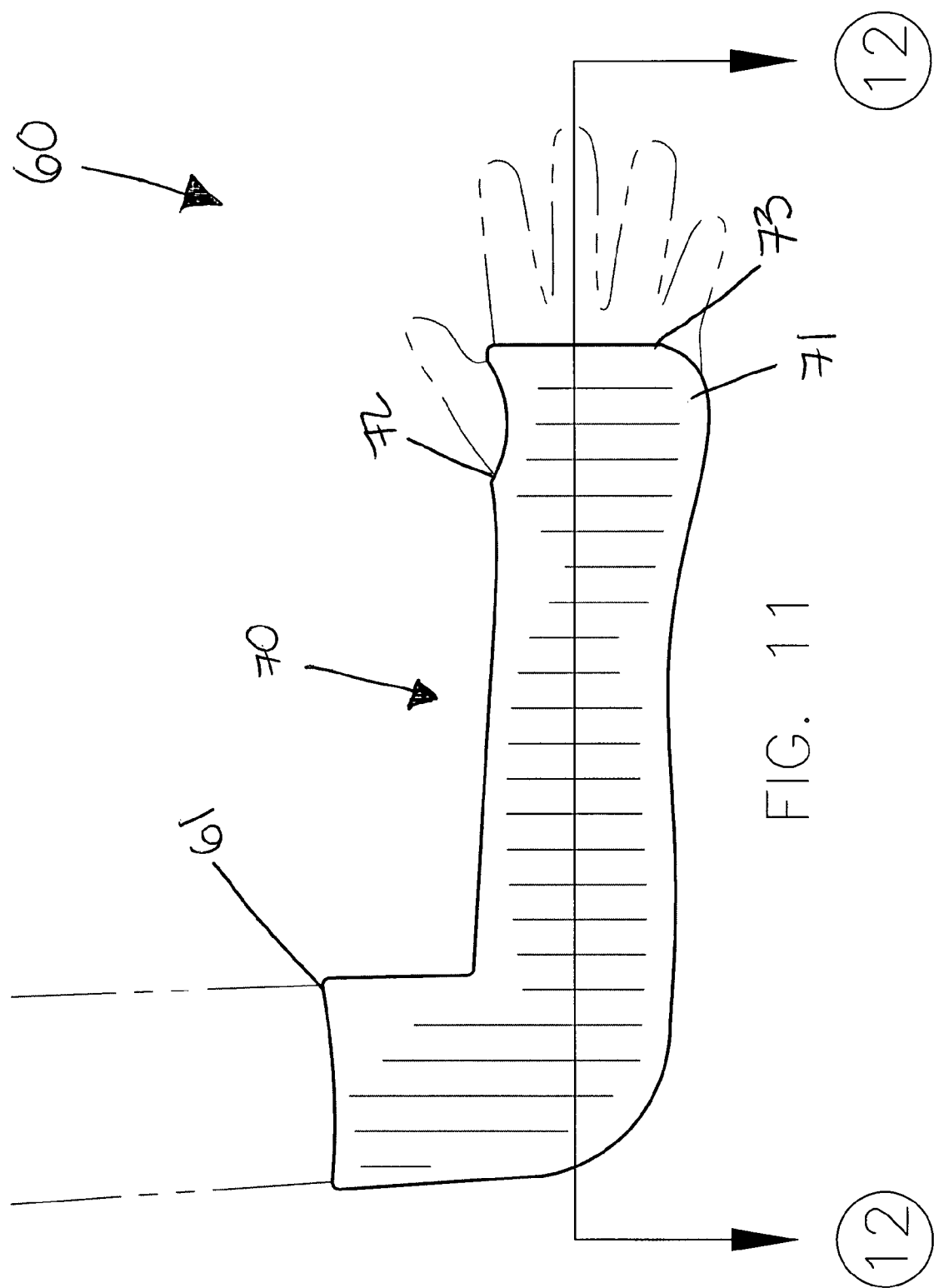
FIG. 11 is a side elevational view of a third one of the arm protective sleeves in accordance with the present invention.

Referring to FIGS. 11 and 12, a first one of the second protective sleeves 70 includes a distal end 71 provided with first 72 and second 73 orifices formed therein. The first orifice 72 is advantageously positioned along a top surface of the distal end and the second orifice 73 is positioned along a lateral surface of the distal end. A thumb of the user is conveniently passed through the first orifice 72 and remaining metacarpals of the user are passed through the second orifice 73. The orifices 72, 73 allow a user to effectively protect a user cast while still allowing a user to have use of his hand.

Figure 9:
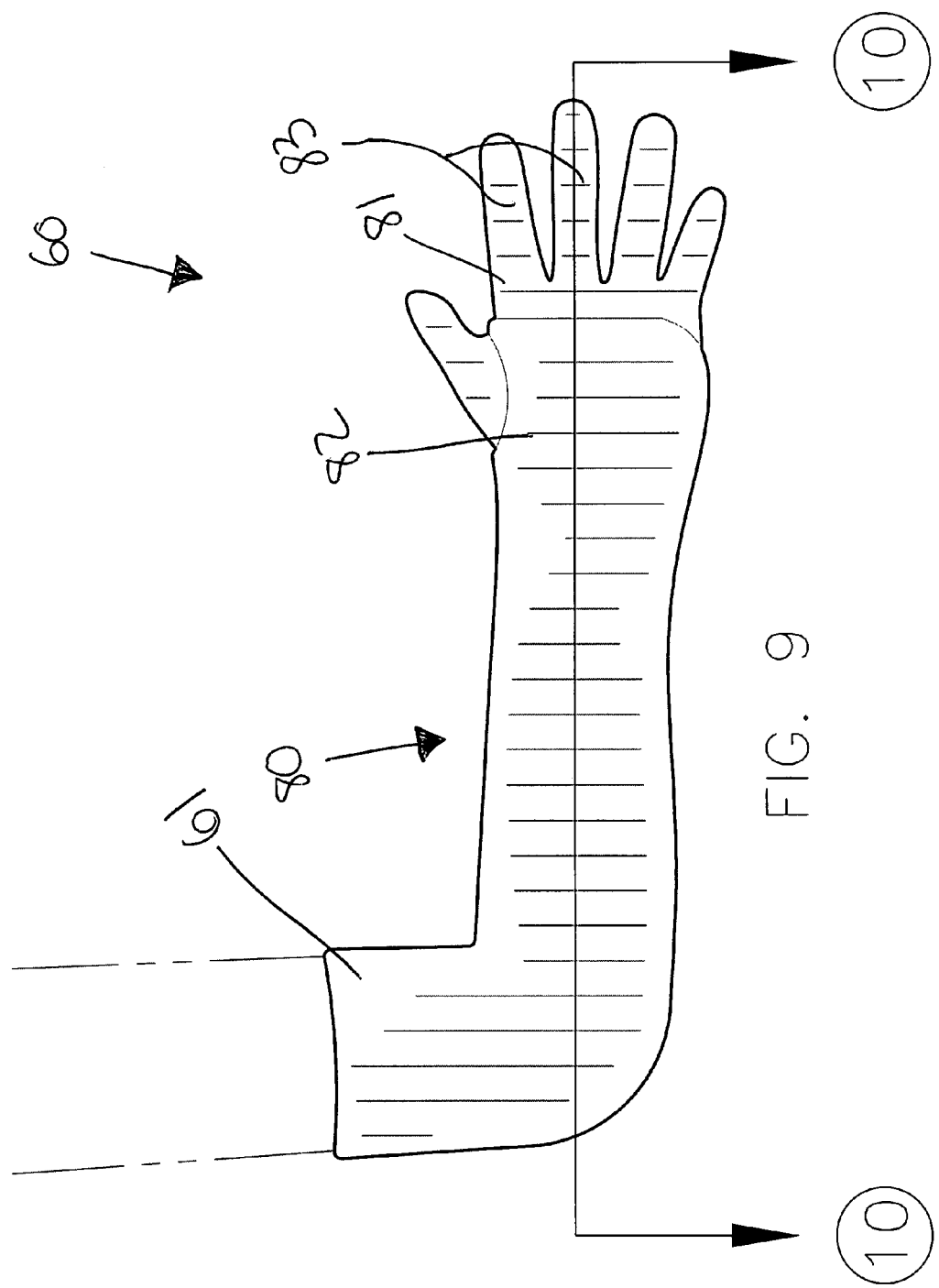
FIG. 9 is a side elevational view of a second one of the arm protective sleeves in accordance with the present invention.
Figure 10:
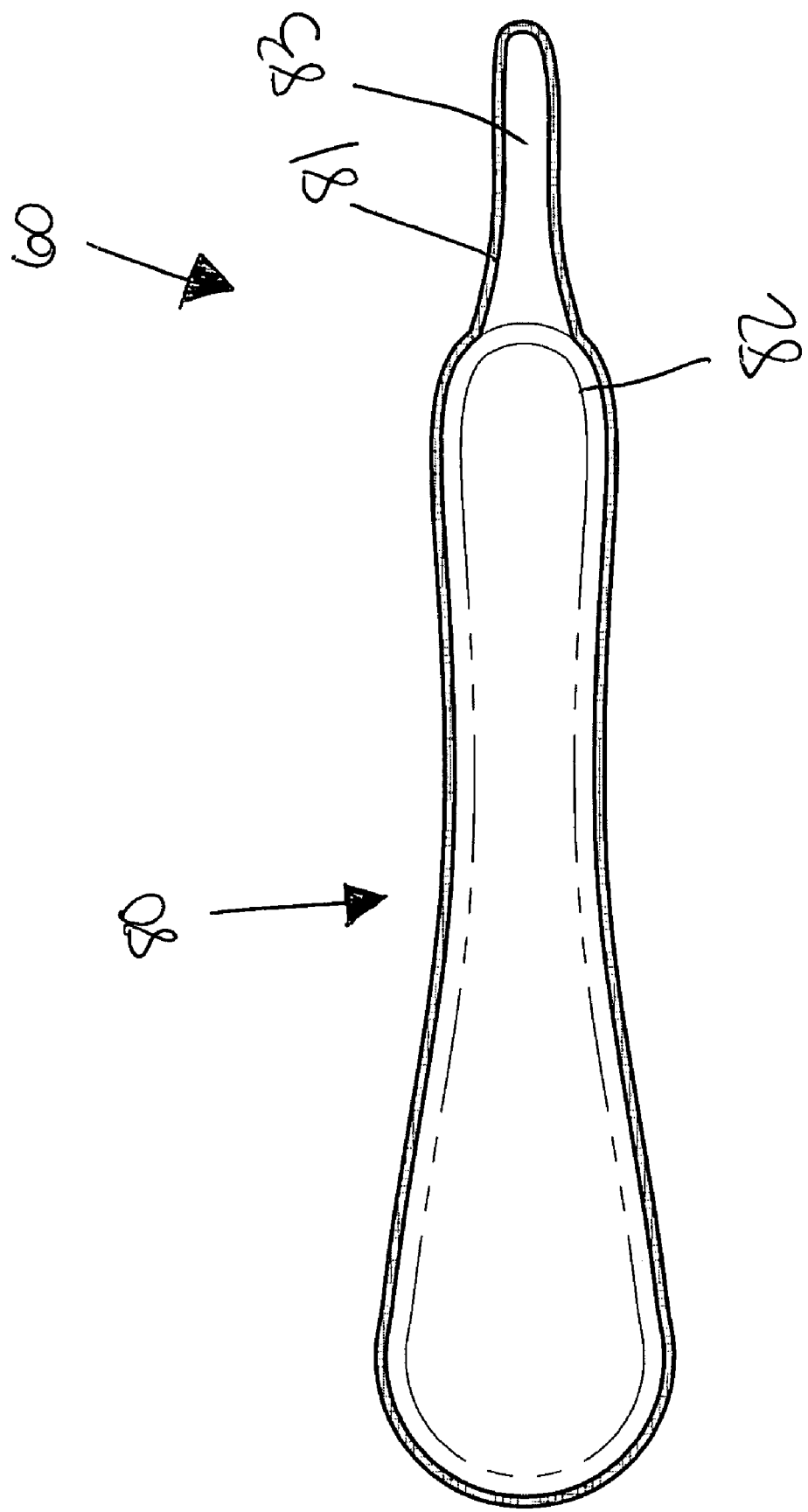
FIG. 10 is a cross sectional view of a second one of the arm protective sleeves taken along line 10-10 as shown in FIG. 9.

Referring to FIGS. 9 and 10, a second one of the second protective sleeves 80 effectively includes a glove 81 monolithically formed with a distal end 82 thereof and is removably positioned over an entire surface area of a hand of the user for prohibiting water from contacting the user epithelial tissue. Such a glove 81 includes a plurality of spaced ducts 83 independently fitted over each metacarpal of the user hand which is crucial for advantageously allowing mobile movement of the metacarpals. The glove 81 allows a user to protect a user cast even while doing tasks which require full submersion of the hands and arm.

Figure 7:
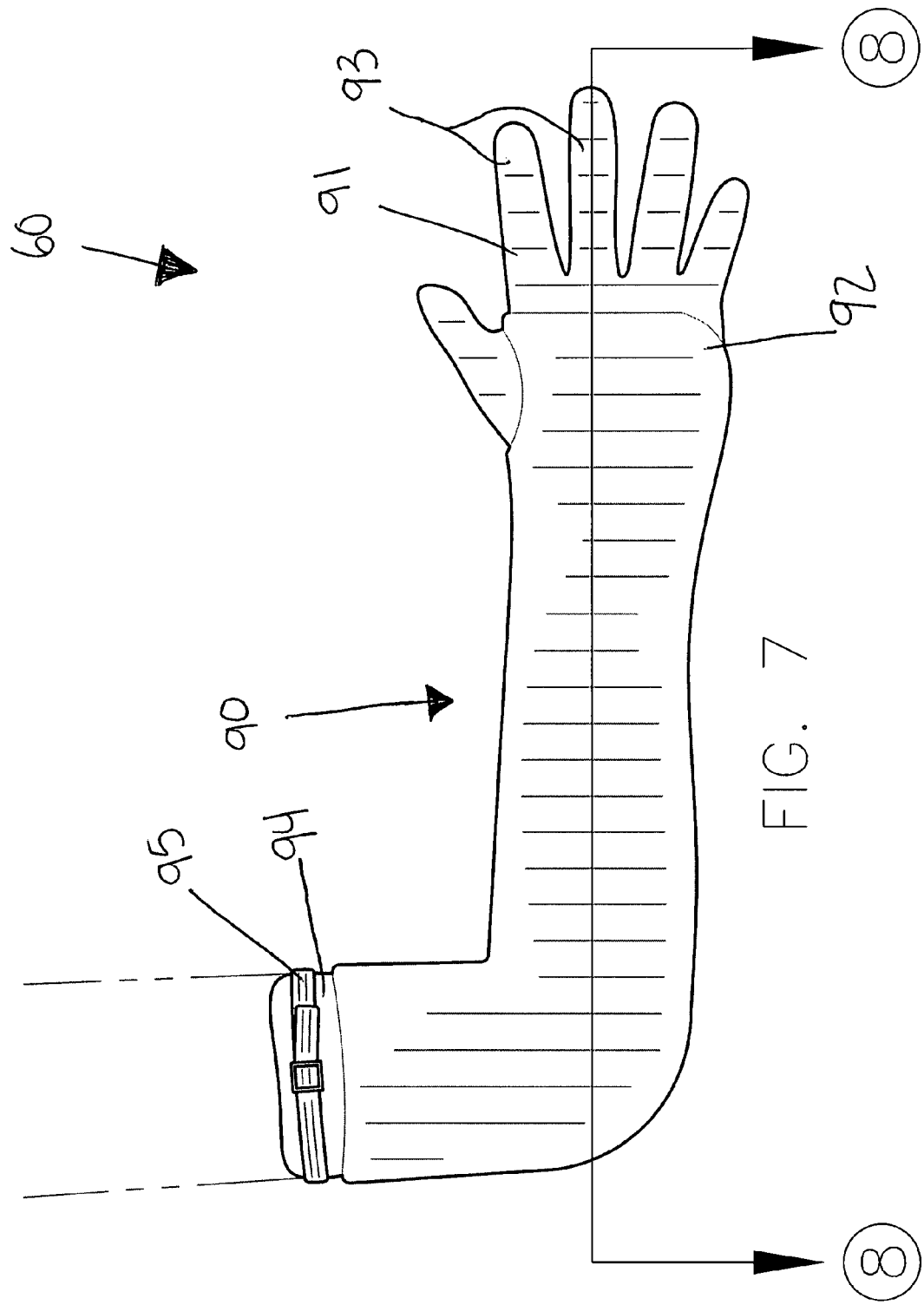
FIG. 7 is a side elevational view of a third one of the arm protective sleeves in accordance with the present invention.
Figure 8:
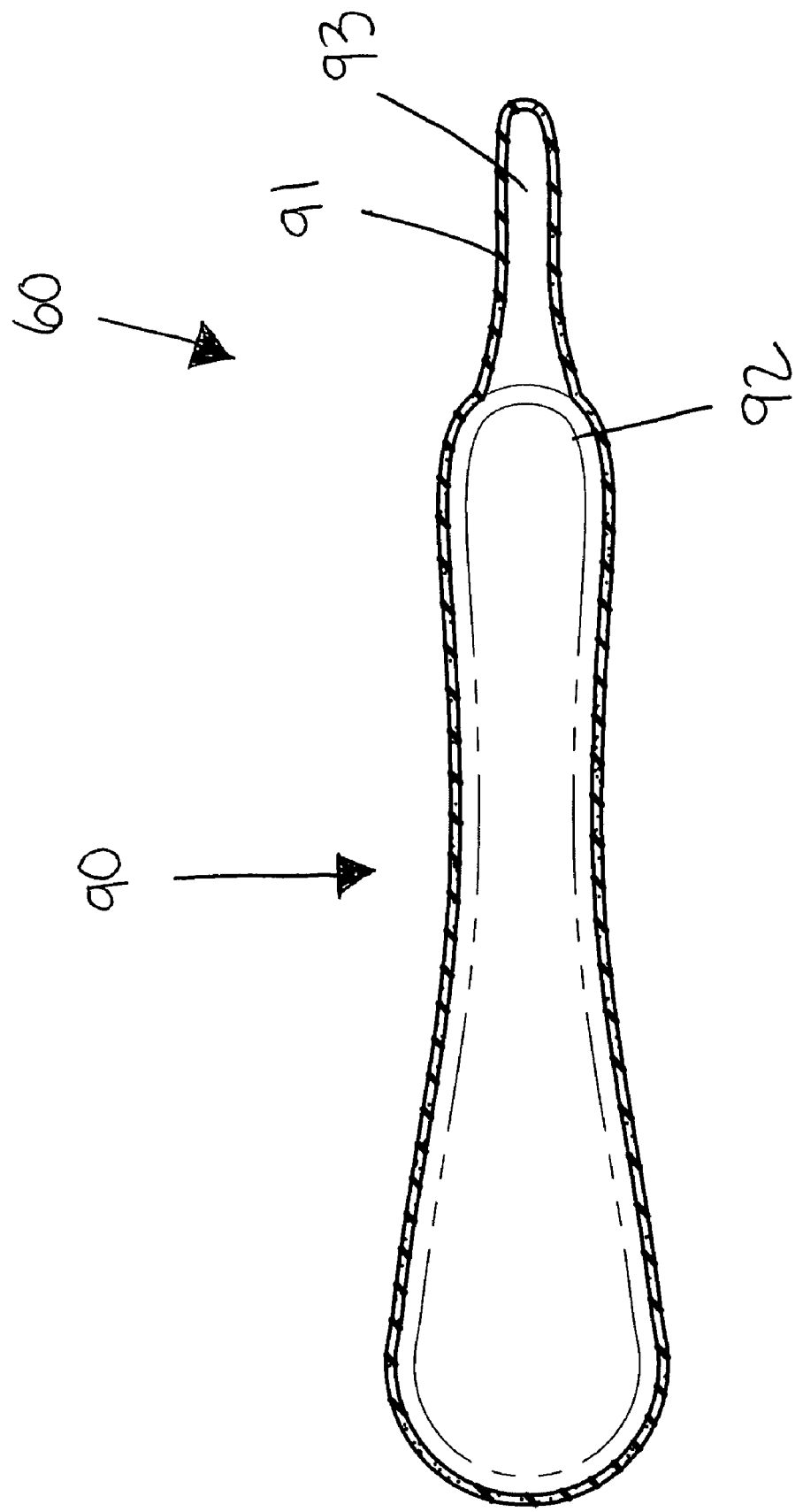
FIG. 8 is a cross sectional view of a third one of the arm protective sleeves taken along line 8-8 as shown in FIG. 7.

Referring to FIGS. 7 and 8, a third one of the second protective sleeves 90 conveniently includes a glove 91 monolithically formed with a distal end 92 thereof and is removably positioned over an entire surface area of a hand of the user which is vital for prohibiting water from contacting the user epithelial tissue. Such a glove 91 effectively includes a plurality of spaced ducts 93 independently fitted over each metacarpal of the user hand for allowing mobile movement of the metacarpals. The glove 91 further includes an ancillary extension 94 monolithically formed with the proximal end. Such an ancillary section 94 advantageously maintains direct contact with epithelial tissue of the user and is spaced from the existing arm cast. The ancillary section 94 has a diameter smaller than a diameter of the proximal end for assisting to anchor the third one of the second protective sleeves 90 above an upper most end of the existing arm cast during extended time periods. An elastic strap 95 is securely wrapped about the ancillary extension 94 in such a manner that the elastic strap 95 conveniently maintains a water-tight seal against the epithelial of the user and thereby prevents water from seeping into the existing arm cast.

The elastic strap 95 provides the unexpected benefit of allowing a user to shower or travel in the rain without being concerned that water may permeate a user cast. Such an elastic strap 95 effectively remains tight around the cast area thereby preventing any water leakage. In addition, the thickness of each protective covering assures a secure fit over a user cast and thereby allows the user to move about freely and comfortably. Such benefits overcome the prior art shortcomings.

In use, a method for shielding existing foot and arm casts worn by a user during a healing period includes the steps of: providing a plurality of first protective sleeves 20; providing a plurality of second protective sleeves 30; and selecting an appropriate sleeve from the first and second pluralities of protective sleeves respectively. If the selected sleeve is chosen from the first protective sleeves 20, then the method includes the steps of: fitting the selected sleeve over an entire surface area of the existing foot cast by removably positioning a bottom end 21 of the selected protective sleeve over an entire foot of the user and further by situating an open top end 22 of the selected protective sleeve subjacent to a knee of the user. If the selected sleeve is chosen from the second protective sleeves 30, then the method includes the steps of: fitting the selected sleeve over an entire surface area of the existing arm cast by situating an open proximal end 22 of the selected sleeve above an arm of the user.

In use, when a user selects among the first protective sleeves 20 for use, the method further includes the steps of: maintaining direct contact with the entire outer surface of the existing foot cast by positioning a uniform thickness of the selected protective sleeve against the existing foot cast; and directly, without the use of intervening elements, engaging a pad 23 to a bottom surface of the bottom end 21 of the selected protective sleeve. Such a pad 23 extends downwardly from the bottom end and forms a barrier between a ground surface and the bottom end 21 of the selected protective sleeve such that the pad 23 is intercalated between the bottom end of the selected protective sleeve and the ground surface during walking procedures.

In use, the method in using the first set of protective sleeves 30 further includes the steps of providing an ancillary extension 41 monolithically formed with the open top end 22 of the selected protective sleeve by ensuring that the ancillary extension 41 maintains direct contact with epithelial tissue of the user and remains spaced from the existing foot cast. Such an ancillary extension 41 has a diameter smaller than a diameter of the open top end 22 for assisting to anchor the selected protective sleeve above an upper most end of the foot cast during extended time periods. The steps further include: securely wrapping an elastic strap 42 about the ancillary extension 41 in such a manner that the elastic strap 42 maintains a water-tight seal against the epithelial of the user and thereby prevents water from seeping into the existing foot cast; and detaching the elastic strap from the selected protective sleeve after a healing process is completed.

In use, the method in using the first set of protective sleeves further includes the steps of: forming a first orifice 51 within the bottom end of the selected protective sleeve; and forming a second orifice 52 within the pad associated therewith. Such orifices are vertically aligned and in direct communication for allowing an existing protective protrusion of the existing foot cast to penetrate outwardly from the selected protective sleeve and thereby absorb impact forces exerted on the foot of the user during walking procedures.

In use, the method in using the second set of protective sleeves includes the steps of: forming first and second orifices 51, 52 within a distal end of the selected protective sleeve. Such a first orifice 51 is positioned along a top surface of the distal end and such a second orifice 52 is positioned along a lateral surface of the distal end.

In use, the method in using the second set of protective sleeves 60 further includes the steps of: passing a thumb of the user through the first orifice 72; passing remaining metacarpals of the user through the second orifice 73; providing a glove 81 that is monolithically formed with a distal end 82 of the selected protective sleeve; and removably positioning the glove 81 over an entire surface area of a hand of the user for prohibiting water from contacting the user epithelial tissue. Such a glove 81 includes a plurality of spaced ducts 83 independently fitted over each metacarpal of the user hand for allowing mobile movement of the metacarpals.

In use, the method in using the second set of protective sleeves further includes the steps of providing an ancillary extension 94 monolithically formed with a proximal end of the selected protective sleeve by ensuring that the ancillary extension 94 maintains direct contact with epithelial tissue of the user and remains spaced from the existing arm cast. Such an ancillary extension 94 has a diameter smaller than a diameter of the proximal end for assisting to anchor the selected protective sleeve above an upper most end of the arm cast during extended time periods. The steps further include: securely wrapping an elastic strap 95 about the ancillary extension 94 in such a manner that the elastic strap 95 maintains a water-tight seal against the epithelial of the user and thereby prevents water from seeping into the existing arm cast; and detaching the elastic strap 95 from the selected protective sleeve after a healing process is completed.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A set of protective cast accessories for shielding existing foot and arm casts worn by a user during a healing period, said set of protective cast accessories comprising:
   a plurality of first protective sleeves adapted to fit over an entire surface area of the existing foot cast, each of said first protective sleeves having a bottom end adapted to be removably positioned over an entire foot of the user and further having an open top end adapted to be situated subjacent to a knee of the user, each of said first protective sleeves having a uniform thickness throughout an entire surface area thereof and maintaining direct contact with the entire outer surface of the existing foot cast, each of said first protective sleeves including a pad directly engaged with a bottom surface of said bottom end, said pad extending downwardly from said bottom end and forming a barrier between a ground surface and said bottom end of said first protective sleeves such that said pad is intercalated between said bottom end of said first protective sleeves and the ground surface during walking procedures; and
   a plurality of second protective sleeves suitable adapted to fit over an entire surface area of the existing arm cast, each of said second protective sleeves having an open proximal end adapted to be situated above an arm of the user, each of said second protective sleeves having a uniform thickness throughout an entire surface area thereof and maintaining direct contact with the entire outer surface of the existing arm cast;
   wherein one of said first protective sleeves comprises
   a first orifice formed within said bottom end thereof; and
   a second orifice formed within said pad associated therewith, each of said first and second orifices being vertically aligned and in direct communication for allowing an existing protective protrusion of the existing foot cast to penetrate outwardly from said second one of said first protective sleeves and thereby adapted to absorb impact forces exerted on the foot of the user during walking procedures;
   wherein each of said first and second protective sleeves has a smooth outer surface.

2. The set of protective cast accessories of claim 1, wherein a bottom end of a first one of said first protective sleeves is closed and is adapted to completely shelter the user foot from external fluids and debris.

3. The set of protective cast accessories of claim 1, wherein a second one of said first protective sleeves comprises:
   an ancillary extension monolithically formed with said open top end thereof, said ancillary extension adapted to maintainer direct contact with epithelial tissue of the user and spaced from the existing foot cast, said ancillary extension having a diameter smaller than a diameter of said open top end for assisting to anchor said first one of said first protective sleeves above an upper most end of said foot cast during extended time periods; and
   an elastic strap securely wrapped about said ancillary extension in such a manner that said elastic strap is adapted to be maintain a water-tight seal against the epithelial of the user and thereby prevents water from seeping into the existing foot cast, said elastic strap being detachable from said first one of said first protective sleeves.

4. The set of protective cast accessories of claim 1, wherein a first one of said second protective sleeves comprises: a distal end provided with first and second orifices formed therein, said first orifice being positioned along a top surface of said distal end and said second orifice being positioned along a lateral surface of said distal end.

5. The set of protective cast accessories of claim 1, wherein a second one of said second protective sleeves comprises: a glove monolithically formed with a distal end thereof and adapted to be removably positioned over an entire surface area of a hand of the user for prohibiting water from contacting the user epithelial tissue, said glove including a plurality of spaced ducts independently adapted to fit over each metacarpal of the user hand for allowing mobile movement of the metacarpals.

6. The set of protective cast accessories of claim 1, wherein a third one of said second protective sleeves comprises:
   a glove monolithically formed with a distal end thereof and adapted to be removably positioned over an entire surface area of a hand of the user for prohibiting water from contacting the user epithelial tissue, said glove including a plurality of spaced ducts independently adapted to fit over each metacarpal of the user hand for allowing mobile movement of the metacarpals;
   an ancillary extension monolithically formed with said proximal end, said ancillary section adapted to maintaining direct contact with epithelial tissue of the user and being spaced from the existing arm cast, said ancillary section having a diameter smaller than a diameter of said proximal end for assisting to anchor said third one of said second protective sleeves above an upper most end of said existing arm cast during extended time periods; and an elastic strap securely wrapped about said ancillary extension in such a manner that said elastic strap is adapted to maintain a water-tight seal against the epithelial of the user and thereby prevents water from seeping into the existing arm cast.

7. A method for shielding existing foot and arm casts worn by a user during a healing period, said method comprising the steps of:
   a. providing a plurality of first protective sleeves;
   b. providing a plurality of second protective sleeves;
   c. selecting an appropriate sleeve from said first and second pluralities of protective sleeves respectively;
   d. if said selected sleeve is chosen from said first protective sleeves, then fitting said selected sleeve over an entire surface area of the existing foot cast by removably positioning a bottom end of said selected protective sleeve over an entire foot of the user and further by situating an open top end of said selected protective sleeve subjacent to a knee of the user; and
   e. if said selected sleeve is chosen from said second protective sleeves, then fitting said selected sleeve over an entire surface area of the existing arm cast by situating an open proximal end of said selected sleeve above an arm of the user;
   wherein step d. comprises the steps of:
      i. maintaining direct contact with the entire outer surface of the existing foot cast by positioning a uniform thickness of said selected protective sleeve against the existing foot cast; and
      ii. directly engaging a pad to a bottom surface of said bottom end of said selected protective sleeve, said pad extending downwardly from said bottom end and forming a barrier between a ground surface and said bottom end of said selected protective sleeve such that said pad is intercalated between said bottom end of said selected protective sleeve and the ground surface during walking procedures;
   wherein step d. comprises the steps of:
      iii. forming a first orifice within said bottom end of said selected protective sleeve; and
      iv. forming a second orifice within said pad associated therewith, each of said first and second orifices being vertically aligned and in direct communication for allowing an existing protective protrusion of the existing foot cast to penetrate outwardly from said selected protective sleeve and thereby absorb impact forces exerted on the foot of the user during walking procedures.

8. The method of claim 7, wherein step d. comprises the steps of:
   i. providing an ancillary extension monolithically formed with said open top end of said selected protective sleeve by ensuring that said ancillary extension maintains direct contact with epithelial tissue of the user and remains spaced from the existing foot cast, said ancillary extension having a diameter smaller than a diameter of said open top end for assisting to anchor said selected protective sleeve above an upper most end of said foot cast during extended time periods;
   ii. securely wrapping an elastic strap about said ancillary extension in such a manner that said elastic strap maintains a water-tight seal against the epithelial of the user and thereby prevents water from seeping into the existing foot cast; and
   iii. detaching said elastic strap from said selected protective sleeve after a healing process is completed.

9. The method of claim 7, wherein step e. comprises the steps of:
   i. forming first and second orifices within a distal end of said selected protective sleeve, said first orifice being positioned along a top surface of said distal end and said second orifice being positioned along a lateral surface of said distal end.

10. The method of claim 9, wherein step e. further comprises the steps of:
   i. passing a thumb of the user through said first orifice; and
   ii. passing remaining metacarpals of the user through said second orifice.

11. The method of claim 7, wherein step e. comprises the steps of:
   i. providing a glove that is monolithically formed with a distal end of said selected protective sleeve; and
   ii. removably positioning said glove over an entire surface area of a hand of the user for prohibiting water from contacting the user epithelial tissue, said glove including a plurality of spaced ducts independently fitted over each metacarpal of the user hand for allowing mobile movement of the metacarpals.

12. The method of claim 7, wherein step e. comprises the steps of:
   i. providing an ancillary extension monolithically formed with a proximal end of said selected protective sleeve by ensuring that said ancillary extension maintains direct contact with epithelial tissue of the user and remains spaced from the existing arm cast, said ancillary extension having a diameter smaller than a diameter of said proximal end for assisting to anchor said selected protective sleeve above an upper most end of said arm cast during extended time periods;
   ii. securely wrapping an elastic strap about said ancillary extension in such a manner that said elastic strap maintains a water-tight seal against the epithelial of the user and thereby prevents water from seeping into the existing arm cast; and
   iii. detaching said elastic strap from said selected protective sleeve after a healing process is completed.

* * * * *